US012661218B2

(12) United States Patent　　(10) Patent No.:　US 12,661,218 B2
Auld et al.　　　　　　　　　　　　(45) Date of Patent:　　Jun. 23, 2026

(54) HAPTIC OPTIC MANAGEMENT SYSTEM UTILIZING ROTATING CAMS

(71) Applicant: Alcon Inc., Fribourg (CH)

(72) Inventors: Jack Robert Auld, Laguna Niguel, CA (US); Matthew Braden Flowers, Aliso Viejo, CA (US); Matthew Douglas Mccawley, San Clemente, CA (US); Andrew Thomas Schieber, Tustin, CA (US); Sudarshan B. Singh, Euless, TX (US); Marcus Antonio Souza, Costa Mesa, CA (US)

(73) Assignee: Alcon Inc., Fribourg (CH)

( * ) Notice: Subject to any disclaimer, the term of this patent is extended or adjusted under 35 U.S.C. 154(b) by 738 days.

(21) Appl. No.: 18/055,671

(22) Filed: Nov. 15, 2022

(65) Prior Publication Data

US 2023/0070765 A1　　　Mar. 9, 2023

Related U.S. Application Data

(62) Division of application No. 16/713,064, filed on Dec. 13, 2019, now Pat. No. 11,547,556.

(Continued)

(51) Int. Cl.
*A61F 2/16*　　　　(2006.01)
*A61F 2/48*　　　　(2006.01)

(52) U.S. Cl.
CPC ............ *A61F 2/1678* (2013.01); *A61F 2/167* (2013.01); *A61F 2002/1683* (2013.01); *A61F 2/484* (2021.08)

(58) Field of Classification Search
CPC ........ A61F 2/1678; A61F 2/167; A61F 2/484; A61F 2002/1683; A61F 2/1662; A61F 2/1613; A61F 9/00736; A61F 2002/1681
See application file for complete search history.

(56) References Cited

U.S. PATENT DOCUMENTS

2007/0270945 A1　11/2007　Kobayashi et al.
2008/0077237 A1　3/2008　Isaacs et al.
(Continued)

FOREIGN PATENT DOCUMENTS

JP　　2010-504165 A　　2/2010
JP　　2015-171529 A　　10/2015
(Continued)

*Primary Examiner* — Ashley L Fishback
*Assistant Examiner* — Chima U Igboko
(74) *Attorney, Agent, or Firm* — Patterson + Sheridan, LLP

(57) ABSTRACT

Systems, methods, and devices for inserting an intraocular lens (IOL) into an eye may be provided. An example haptic optic management system may comprise a first cam assembly comprising a first cam body portion, an opening in the first cam body portion, and haptic folder arms disposed in the opening. The haptic optic management system may further comprise a second cam assembly positioned on one side of the first cam assembly, wherein the second cam assembly comprises a second cam body portion, an opening in the second cam body portion, and optic folders disposed in the opening. The haptic optic management system may further comprise a central plate for holding an intraocular lens in the opening of the second cam body portion, wherein the central plate is disposed between the first cam assembly and the second cam assembly.

4 Claims, 14 Drawing Sheets

Related U.S. Application Data

(60) Provisional application No. 62/779,058, filed on Dec. 13, 2018.

(56) References Cited

U.S. PATENT DOCUMENTS

| | | | |
|---|---|---|---|
| 2010/0036385 A1 | 2/2010 | Isaacs et al. | |
| 2012/0158007 A1 | 6/2012 | Brown et al. | |
| 2013/0018460 A1 | 1/2013 | Anderson | |
| 2013/0103040 A9* | 4/2013 | Kappelhof | A61F 2/1664 |
| | | | 606/107 |
| 2014/0074107 A1 | 3/2014 | Biddle et al. | |
| 2015/0320549 A1 | 11/2015 | Cole et al. | |
| 2016/0331587 A1* | 11/2016 | Yamada | A61F 2/1678 |

FOREIGN PATENT DOCUMENTS

| | | | |
|---|---|---|---|
| WO | 2004087019 A1 | 10/2004 | |
| WO | WO2010093593 A1 | 8/2010 | |
| WO | 2015125905 A1 | 8/2015 | |
| WO | 2018221434 A1 | 12/2018 | |

* cited by examiner

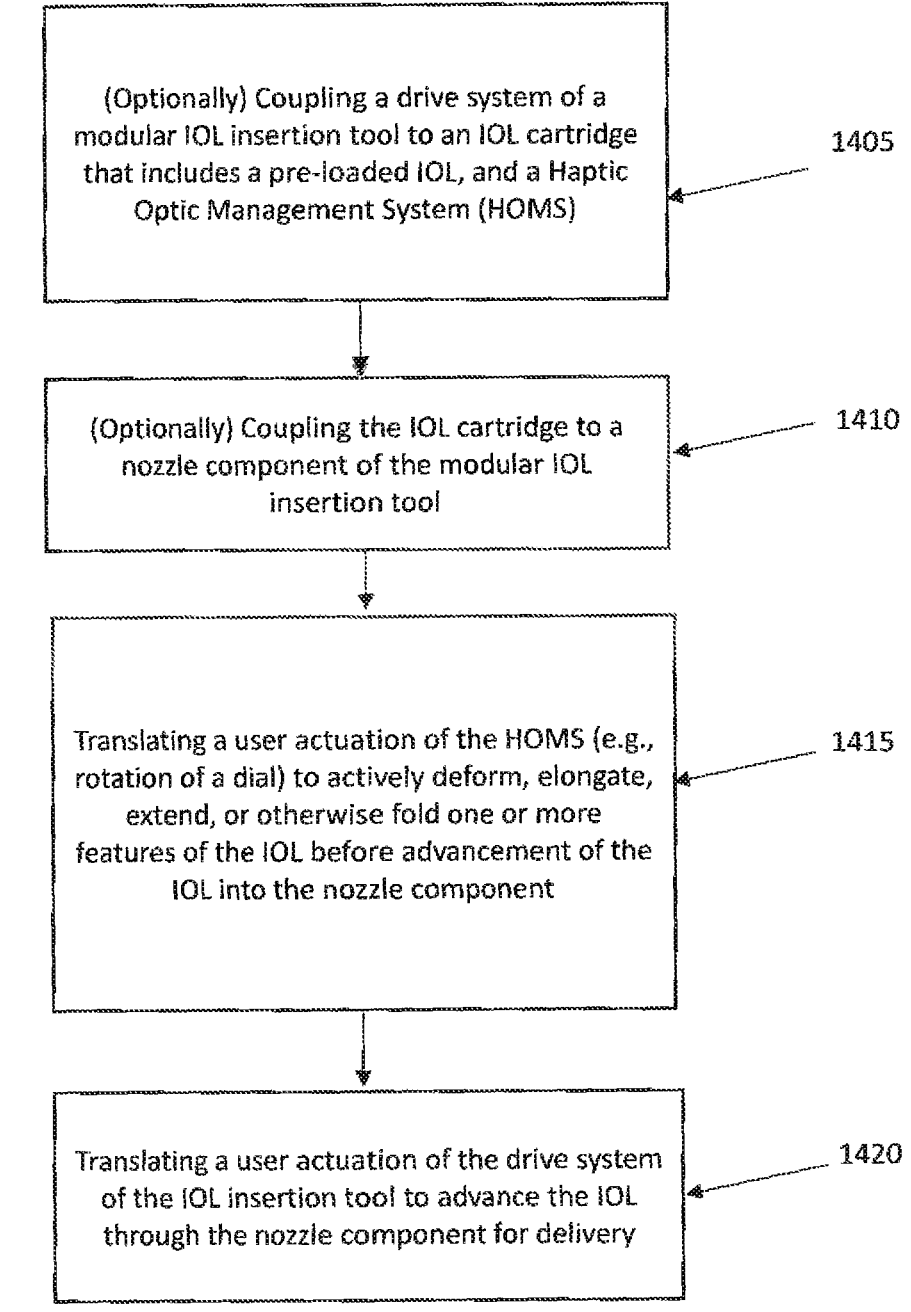

1400

(Optionally) Coupling a drive system of a modular IOL insertion tool to an IOL cartridge that includes a pre-loaded IOL, and a Haptic Optic Management System (HOMS)

1405

(Optionally) Coupling the IOL cartridge to a nozzle component of the modular IOL insertion tool

1410

Translating a user actuation of the HOMS (e.g., rotation of a dial) to actively deform, elongate, extend, or otherwise fold one or more features of the IOL before advancement of the IOL into the nozzle component

1415

Translating a user actuation of the drive system of the IOL insertion tool to advance the IOL through the nozzle component for delivery

HAPTIC OPTIC MANAGEMENT SYSTEM UTILIZING ROTATING CAMS

CROSS-REFERENCE TO RELATED APPLICATIONS

This application is a divisional of U.S. patent application Ser. No. 16/713,064, filed Dec. 13, 2019, which claims priority to and benefit of U.S. Provisional Patent Application No. 62/779,058, filed Dec. 13, 2018. The entire contents of each of these applications are incorporated by reference herein in their entirety

BACKGROUND

The human eye can suffer a number of maladies causing mild deterioration to complete loss of vision. While contact lenses and eyeglasses can compensate for some ailments, ophthalmic surgery may be required for others. Generally, ophthalmic surgery may be classified into posterior segment procedures, such as vitreoretinal surgery, and anterior segment procedures, such as cataract surgery. Vitreoretinal surgery may address many different eye conditions, including, but not limited to, macular degeneration, diabetic retinopathy, diabetic vitreous hemorrhage, macular hole, detached retina, epiretinal membrane, and cytomegalovirus retinitis.

For cataract surgery, a surgical procedure may require incisions and insertion of tools within an eye to replace the clouded natural lens with an intraocular lens ("IOL"). A large incision site may cause a longer post-operation healing time. To reduce this healing time, typical operating procedures have shifted to making incisions of about 2 millimeters in size into the eye. While this smaller size of incision may reduce post-operation healing time, problems such as the size and functionality of the insertion tool may arise as the incision size continues to shrink. Typically, the insertion tool may be pre-loaded with the IOL that may be inserted into the patient's eye once the clouded natural lens is removed. The insertion tool may include a plunger for forcing the IOL out of the nozzle of the insertion tool. The plunger may have additional functions including haptic tucking and folding of the IOL. Once an incision has been made, the insertion tool may be inserted into the eye through the incision, and the folded IOL may be dispensed into the eye by actuation of the plunger. As the incision site decreases, the size of the nozzle of the insertion tool may decrease accordingly.

SUMMARY

In an exemplary aspect, the present disclosure is directed to a haptic optic management system. The haptic optic management system may comprise a first cam assembly comprising a first cam body portion, an opening in the first cam body portion, and haptic folder arms disposed in the opening. The haptic optic management system may further comprise a second cam assembly positioned on one side of the first cam assembly, wherein the second cam assembly comprises a second cam body portion, an opening in the second cam body portion, and optic folders disposed in the opening. The haptic optic management system may further comprise a central plate for holding an intraocular lens in the opening of the second cam body portion, wherein the central plate is disposed between the first cam assembly and the second cam assembly.

In another exemplary aspect, the present disclosure is directed to an insertion tool. The insertion tool may comprise a drive system, wherein the drive system comprises a body. The insertion tool may further comprise a plunger disposed at least partially in the drive system. The insertion tool may further comprise a nozzle. The insertion tool may further comprise a haptic optic management system disposed between the drive system and the nozzle for receiving a distal tip of the plunger. The haptic optic management system may comprise a first cam assembly comprising a first cam body portion, an opening in the first cam body portion, and haptic folder arms disposed in the opening. The haptic optic management system may further comprise a second cam assembly positioned on one side of the first cam assembly, wherein the second cam assembly comprises a second cam body portion, an opening in the second cam body portion, and optic folders disposed in the opening. The haptic optic management system may further comprise a central plate for holding an intraocular lens in the opening of the second cam body portion, wherein the central plate is disposed between the first cam assembly and the second cam assembly.

In another exemplary aspect, the present disclosure is directed to a method of delivering an intraocular lens. The method may comprise rotating a first cam assembly to push haptics of the intraocular lens on top of an optic of the intraocular lens. The method may comprise further rotating the first cam assembly such that the first cam assembly engages a second cam assembly to cause the second cam assembly to rotate while engaging the intraocular lens and cause the optic of the intraocular lens to fold. The method may further comprise actuating a drive system to dispense the intraocular lens through a nozzle and into an eye.

The different aspects may include one or more of the following features. The haptic optic management system may further comprise a base cap disposed on an opposite side of the second cam assembly from the first cam assembly, wherein the base cap comprises holes that receive pins that extends from the haptic folder arms and about which the haptic folder arms rotate. The base cap may further comprise a recessed ring and a raised central surface defined by the recessed ring, wherein the recessed ring receives a raised ring formed at a perimeter of the second cam body portion. The central plate may further comprise a lens face and a channel extending at least partially across the lens face, wherein a first pair of guides and a second pair of guides are each positioned on either side of the channel, wherein the channel receives the optic folders. The optic folders may each comprise a body portion, a tab extending from the body portion to engage the second cam body portion, and a ramp on an opposite end of the body portion from the tab and operable to engage an optic of the intraocular lens when the second cam assembly is actuated, and wherein the optic folders each further comprise protrusions from opposing sides of the body portion that are disposed in protrusion channels formed in at least one of the first pair of guides or the second pair of guides.

The different aspects may further include one or more of the following features. The first cam body portion may comprise an outer perimeter and an inner perimeter. The inner perimeter of the first cam body portion may define the opening in the first cam body portion and one or more cam surfaces operable to engage the haptic folder arms when the first cam assembly is actuated. A cam projection may extend from the first cam body portion at the outer perimeter. The second cam body portion may comprise an outer perimeter and an inner perimeter. The inner perimeter of the second cam body portion may define the opening in the second cam assembly and one or more cam surfaces operable to engage the optic folders when the second cam assembly is actuated. A recessed portion may be formed in the outer perimeter of the second cam body portion. The first cam assembly may be positioned such that the cam projection is disposed in the recessed portion between a first end and a second end of the recessed portion. The haptic folder arms may each have a first end and a second end and comprise a protrusion at the first end and a pin extending from the second end, wherein the protrusion for each of the haptic folder arms extends through corresponding openings in the central plate. The protrusion for each of the haptic folder arms may be operable to follow one or more cam surfaces formed in a perimeter of the opening in the first cam assembly such that that the one or more cam surfaces engage the protrusion to cause rotation of the haptic folder arms when the first cam assembly is actuated. The first cam assembly and the second cam assembly may each disc shaped. An intraocular lens may be disposed on the central plate, wherein the intraocular lens may comprise an optic positioned over a channel formed in a lens face of the central plate, and wherein the intraocular lens may further comprise haptics that extend from the optic across one or more openings in the central plate.

The different aspects may further include one or more of the following features. The plunger may be operable to engage the intraocular lens when the drive system is actuated to dispense the intraocular lens from the nozzle. The drive system may comprise a lever and a pneumatic system. The first cam assembly may comprise a first cam body portion, an opening in the first cam body portion, haptic folder arms disposed in the opening, and one or more cam surfaces formed in a perimeter of the opening of the first cam body portion. The one or more cam surfaces of the first cam assembly may engage the haptic folder arms as the first cam assembly rotates such that the haptic folder arms are rotated to push the haptics on top of the optic. The second cam assembly may comprise a second cam body portion, an opening in the second cam body portion, optic folders disposed in the opening, and one or more cam surfaces formed in a perimeter of the opening in the first cam body portion. The one or more cam surfaces of the second cam assembly may engage the optic folders as the second cam assembly rotates such that the optic folders may be pushed inward toward one another while engaging the intraocular lens to cause the optic to fold in upon itself. The rotating the first cam assembly may comprise applying force to a cam projection that extends from an outer perimeter of the first cam body portion such that the cam projection rides in a recessed portion formed in an outer perimeter of the second body portion. The further rotating the first cam assembly may cause the cam projection to push against an end of the recessed portion causing the second cam assembly to rotate.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

These drawings illustrate certain aspects of some of the embodiments of the present disclosure and should not be used to limit or define the disclosure.

FIG. 14 illustrates a method for preparing an intraocular lens (IOL) for delivery via an IOL insertion tool.

DETAILED DESCRIPTION

Figure 1:
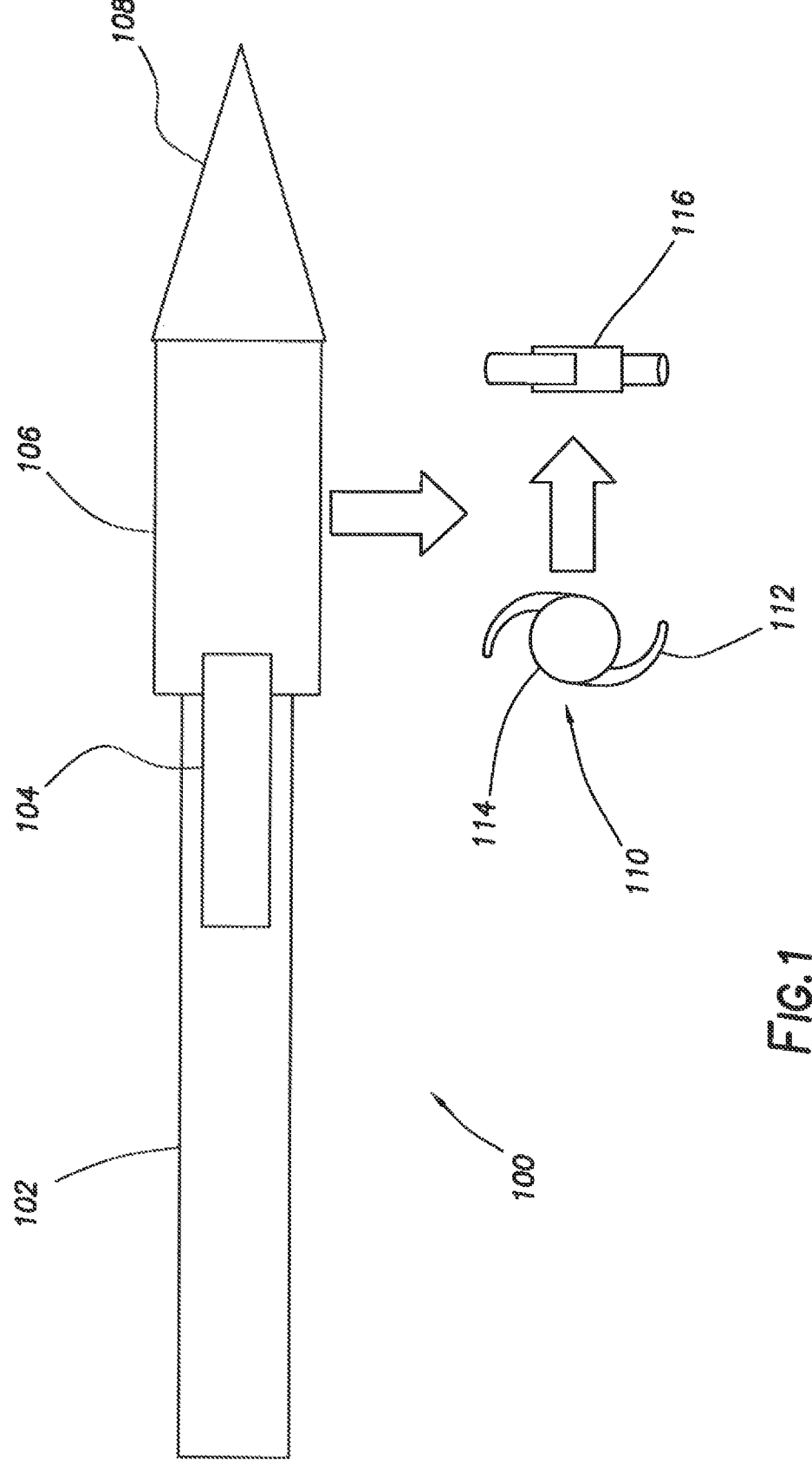
FIG. 1 illustrates a schematic of an example insertion tool operable to deliver an IOL into an eye.

For the purposes of promoting an understanding of the principles of the present disclosure, reference will now be made to the implementations illustrated in the drawings and specific language will be used to describe them. It will nevertheless be understood that no limitation of the scope of the disclosure may be intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with reference to one or more implementations may be combined with the features, components, and/or steps described with reference to other implementations of the present disclosure. For simplicity, in some instances the same reference numbers may be used throughout the drawings to refer to the same or like parts.

The example embodiments described herein generally relate to eye surgery. More particularly, the example embodiments generally relate to systems, methods, and devices for inserting an intraocular lens ("IOL") into an eye. Embodiments may include an insertion tool for preparation and delivery of the IOL into a patient's eye that includes a plunger, a nozzle, and a haptic optic management system. In some embodiments, the haptic management system may fold the IOL and tuck one or more haptics of the IOL. The haptic extends from an optic of the IOL and stabilizes the IOL when disposed within the capsular bag of the eye. After preparation of the IOL, the plunger forces the IOL through the insertion tool and out the nozzle.

FIG. 1 illustrates a schematic of an insertion tool 100. In some embodiments, insertion tool 100 may include a drive system 102, a plunger 104, a haptic optic management system (interchangeably referred to as "HOMS") 106, and a nozzle 108. The drive system 102 may be any system or combination of components operable to actuate the plunger 104. For example, the drive system 102 may utilize a lever and/or pneumatic systems; a manually driven system or component; a hydraulic system; or other device operable to drive the plunger 104 to advance; partially advance; or fully deliver an IOL 110 from the insertion tool 100. The plunger 104 is coupled to the drive system 102. The drive system 102 is operable to actuate the plunger 104. For example, the drive system 102 may be powered by, for example, electrically, mechanically, hydraulically, pneumatically, combinations thereof, or in some other manner. In response to the drive system 102, the plunger 104 moves through the HOMS 106. The HOMS 106 may be located between the drive system 102 and the nozzle 108. In alternate embodiments, the HOMS 106 may be disposed at other locations within the insertion tool 100. In some embodiments, the HOMS 106 may contain an IOL 110 in an unfolded position.

The drive system 102 may be any system, component, or group of components operable to advance an IOL 110 through the insertion tool 100. For example, the drive system 102 include plunger, schematically shown as plunger 104 in FIG. 1, that is operable to engage the IOL 110 disposed within the insertion tool 100 and advance the IOL 110 within the insertion tool 100. In some instances, the plunger 104 is operable to expel the IOL from the insertion tool 100.

In some instances, the drive system 102 may be a manually driven system. That is, in some instances, a user applies a force to cause the drive system 102 to operate. An example drive system 102 includes a plunger 104 that is manually engageable directly or indirectly by a user to push the plunger 1044 through the insertion tool 100. When advanced, the plunger 104 engages an IOL 110 and advances the IOL 110 through the insertion tool 100, which may also include expelling the IOL 110 from the insertion tool 100. A non-limiting example of a manual IOL insertion tool is shown in U.S. Patent Application Publication No. 2016/0256316, the entire contents of which are incorporated herein by reference in its entirety. According to other implementations, the drive system 102 may be an automated system. Example automated drive systems are shown in U.S. Pat. Nos. 8,808,308; 8,308,736; and 8,480,555, the entire contents of each being incorporated herein by reference in their entirety. Still further, other automated drive systems within the scope of the present disclosure are described in U.S. Pat. No. 8,998,983 and U.S. Patent Application Publication No. 2017/0119522, the entire contents of each being incorporated herein by reference in its entirety. While example drive systems are provided as examples, these systems are not intended to be limiting. Rather, any component, group of components, systems, devices, mechanisms, or combinations thereof operable to advance an IOL 110 is within the scope of the present disclosure.

As shown in FIG. 1, the IOL 110 is a single piece IOL that includes an optic 114 and haptics 112 extending from opposing sides of the optic 114. For example, in the example IOL 110 shown in FIG. 1, the haptics 112 are disposed 180° relative to each other along an outer periphery of the optic 114. However, other types of IOLs are within the scope of the disclosure. For example, a multi-piece IOL, in which the optic and one or more haptics are separate components, may also be used.

Figure 2A:
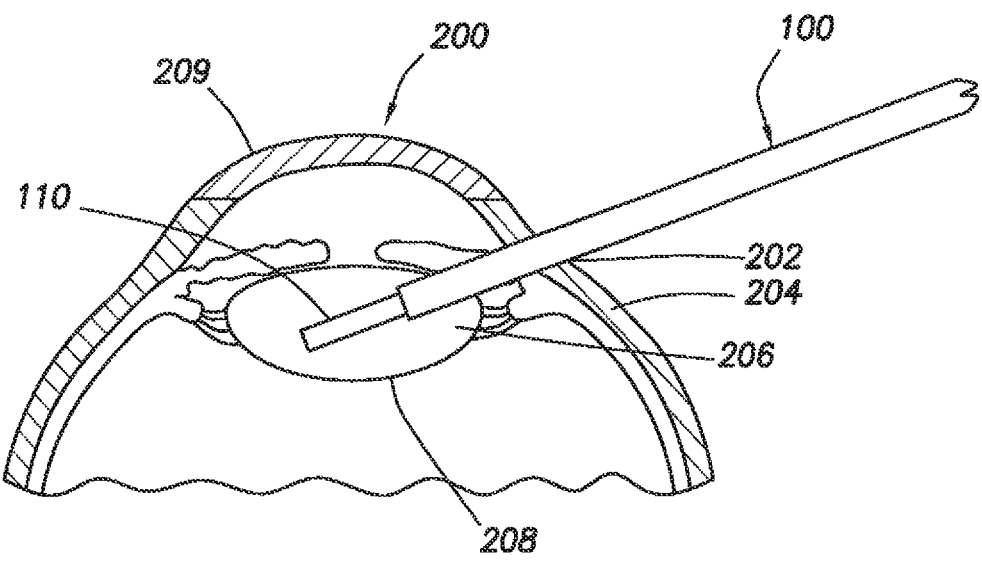
FIG. 2A illustrates an eye in which an IOL is being introduced from an insertion tool.

The IOL 110 may have a shape similar to that of a natural lens of an eye (e.g., eye 200 shown in FIG. 2A). The IOL 110 may be made from a numerous materials including, but not limited to, silicone, acrylic, and/or combinations thereof. Other materials are also contemplated. The haptics 112 extend from a periphery of the optic 114 and function to stabilize the IOL 110 when disposed within an eye.

In some instances, the HOMS 106 may be actuated to tuck the haptics 112 over the optic 114 and fold the optic 114. For example, the HOMS 106 may operate to fold the haptics 112 over the optic 114 and fold the optic 114 over or around the folded haptics 112. The IOL 110 is shown in a folded configuration at 116. The folded configuration 116 of the optic 114 may involve one or more haptics 112 folded relative to the optic 114 and, in some instances, the optic 114 folded relative to one or more of the haptics 112. The plunger 104 may be advanced through the HOMS 106 once the HOMS 106 has folded the IOL 110. As the plunger 104 moves through the HOMS 106, the plunger 104 displaces the folded IOL 110 from the HOMS 106. For example, the plunger 104 may force the folded IOL 110 into and through the nozzle 108.

FIG. 2A illustrates an eye 200 of a patient undergoing an operation with insertion tool 100. As illustrated, the insertion tool 100 dispenses a folded IOL 110 into the eye 200 of a patient. In some embodiments, an incision 202 is made in the eye 200 by a surgeon, for example. For example, in some instances, the incision 202 may be made through the sclera 204 of the eye 200. In other instances, an incision may be formed in the cornea 209 of the eye 200. The incision 202 may be sized to permit insertion of a portion of the insertion tool 100 in order to deliver the folded IOL 110 into the capsular bag 208. For example, in some instances, the size of the incision 202 may have a length less than about 2000 microns (2 millimeters). In other instances, the incision 202 may have a length of from about 0 microns to about 500 microns, from about 500 microns to about 1000 microns, from about 1000 microns to about 1500 microns, or from about 1500 microns to about 2000 microns.

After the incision 202 is made, the insertion tool 100 is inserted through the incision into an interior portion 206 of the eye 200. The insertion tool 100 is actuated to dispense the folded IOL 110 into the capsular bag 208 of the eye 200. Upon dispensation, the folded IOL 110 reverts to an initial, unfolded state, and the IOL 110 settles within the capsular bag 208 of the eye 200, as shown on FIG. 2B. The capsular bag 208 holds the IOL 110 within the eye 200 in a relationship relative to the eye 200 so that the optic 114 refracts light directed to the retina (not shown). The haptics 112 of the IOL 110 engage the capsular bag 208 to secure the IOL 110 therein. After dispensing the IOL 110 into the capsular bag 208, the insertion tool 100 is removed from the eye 200 through the incision 202, and the eye 200 is allowed to heal over a period of time.

Figure 2B:
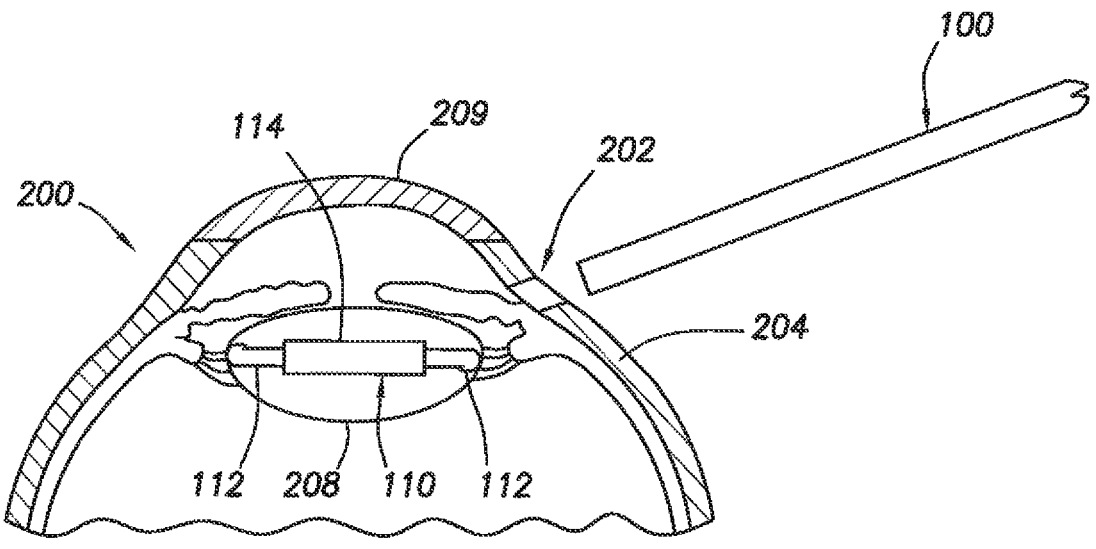
FIG. 2B illustrates the eye shown in FIG. 2A in which the IOL is positioned within the capsular bag of the eye and the insertion tool removed from the eye.
Figure 3:
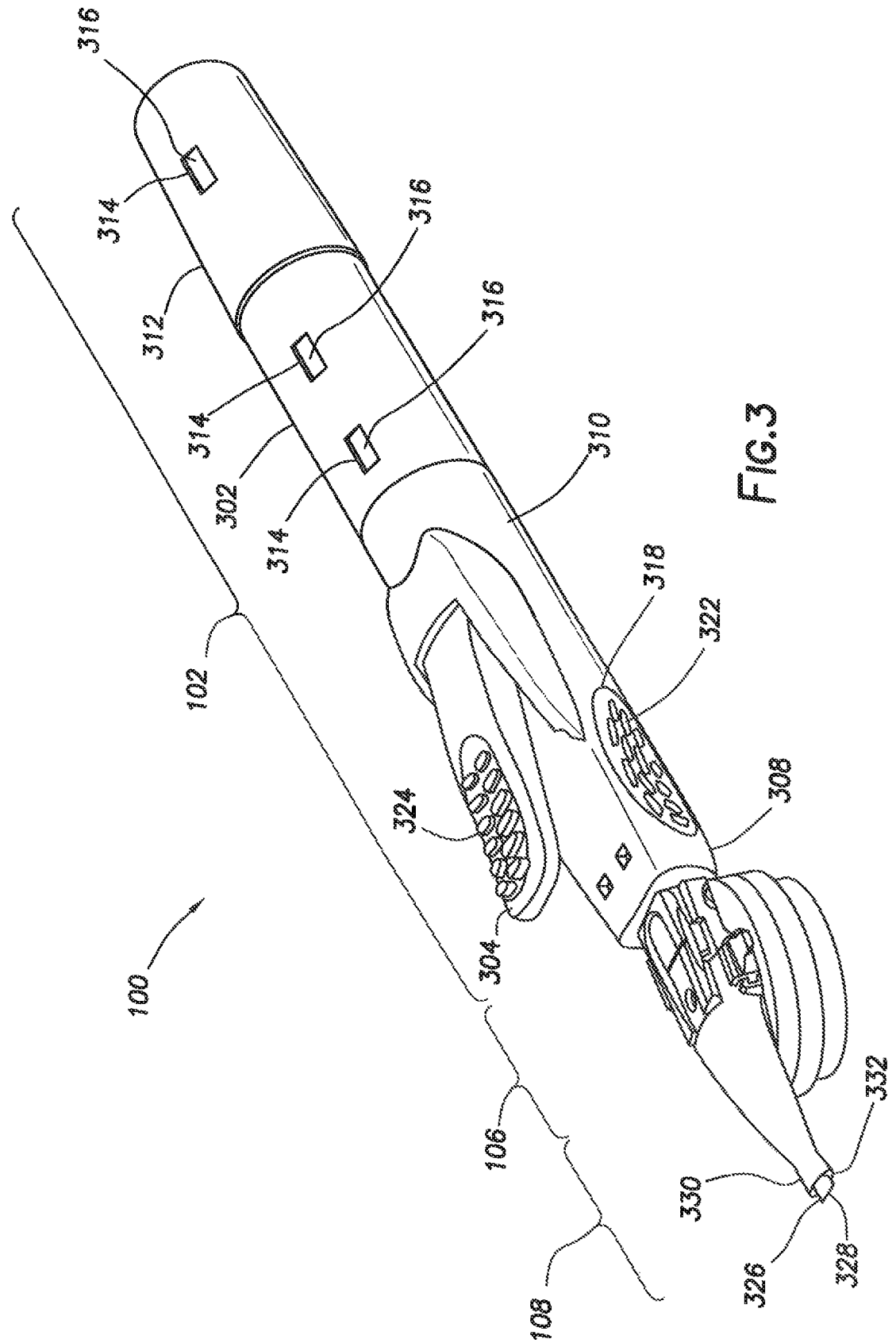
FIG. 3 illustrates a perspective view of another example insertion tool operable to delivery an IOL into an eye.
Figure 4:
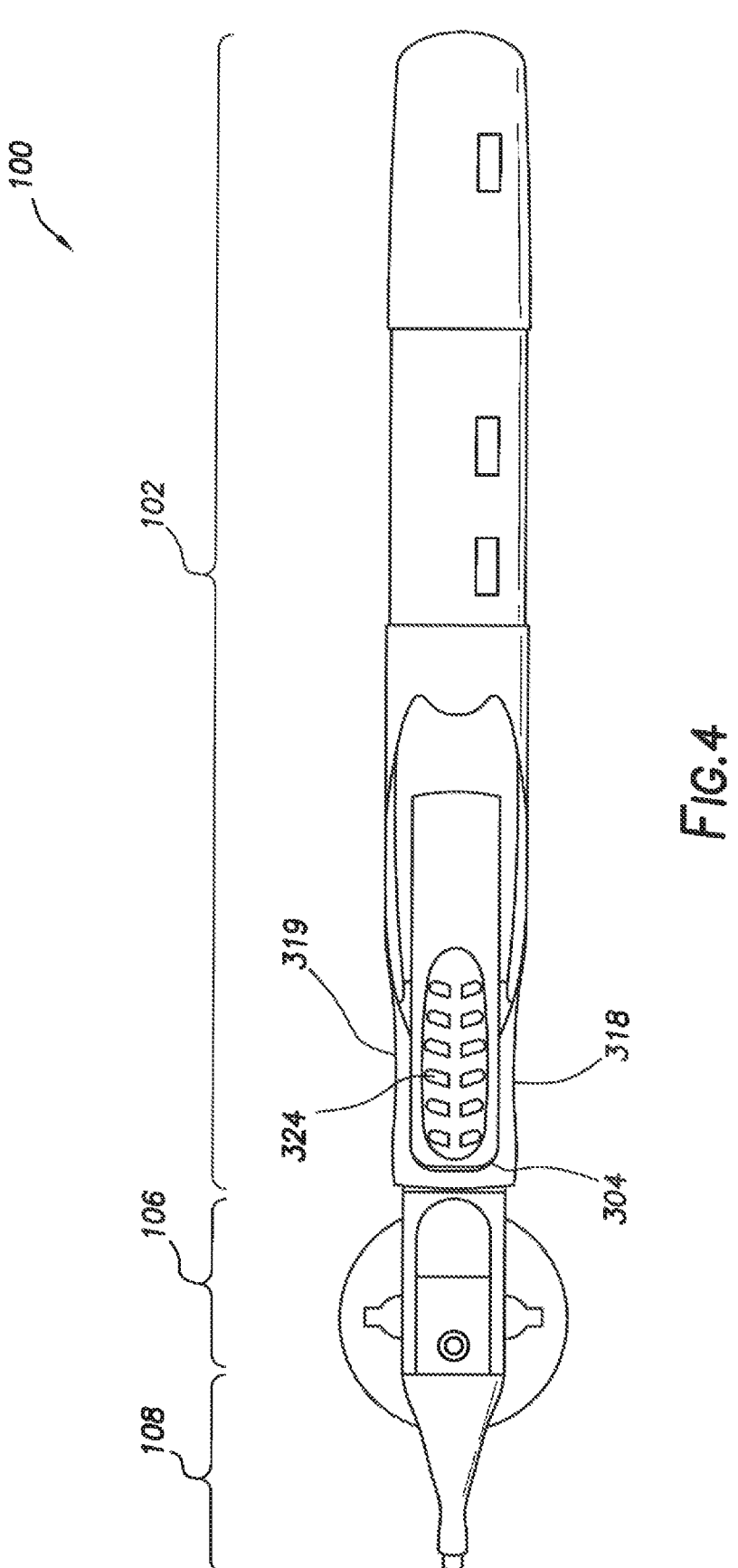
FIG. 4 illustrates a top view of the insertion tool of FIG. 3.
Figure 5:
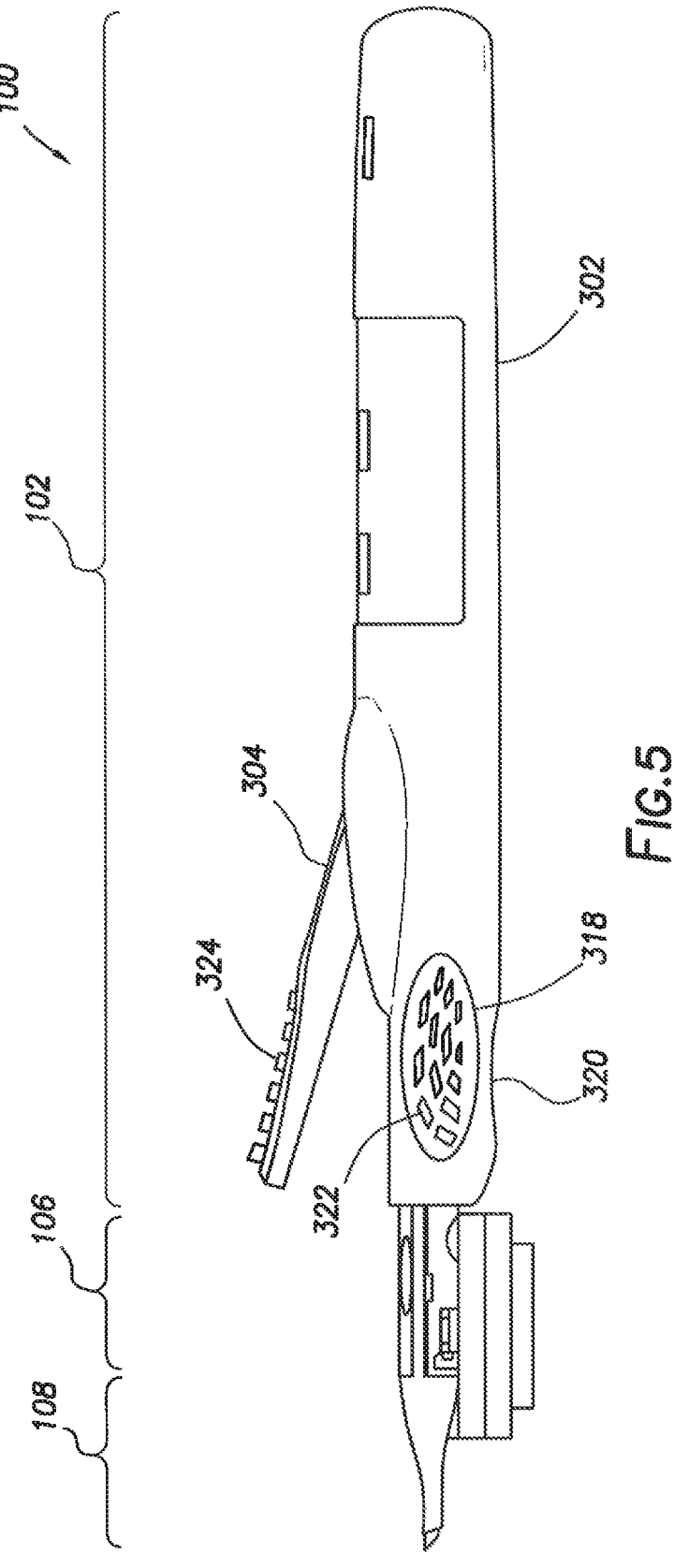
FIG. 5 illustrates a side view of the insertion tool of FIG. 3.

FIGS. 3-5 illustrate an example insertion tool 100 operable to deliver an IOL into the eye (e.g., IOL 110 in eye 200 shown on FIGS. 2A and 2B). As illustrated, the insertion tool 100 includes a drive system 102, a haptic optic management system 106, and a nozzle 108. The insertion tool 100 may also include a plunger, which may be similar to the plunger 104 shown in FIG. 1. In some instances, The plunger 104 may be actuated to advance an IOL, e.g., which may be similar to the IOL 110 shown in FIG. 1, within the insertion tool 100 and, in some cases, dispense the IOL 110 from the insertion tool 100.

Referring to FIG. 3, the drive system 102 includes a body 302 and a lever 304 that may be pivotally coupled to the body 302. The nozzle 108 is coupled to a distal end 308 of the body 302. The HOMS 106 is disposed between the body 302 and the nozzle 108. In some instances, the nozzle 108 may be integrally connected to the body 302. In other instances, the nozzle 108 may be separate from the body 302 and may be coupled to the body 302 via an interlocking relationship. In some instances, the HOMS 106 and the nozzle 108 may be integrally formed. In other instances, the HOMS 106, the nozzle 108, and the body 302 may be integrally formed.

In some instances, the body 302 may have a slender, elongated shape. In some instances, the body 302 may have a first portion 310 and a second portion 312. In some instances, the second portion 312 may be at least partially disposed over the first portion 310. In the example shown, the second portion 312 includes a plurality of apertures 314. A plurality of tabs 316 formed on the first portion 310 are received into the apertures 314 to join the first portion 310 and the second portion 312. The tabs 316 may form an interlocking fit with the apertures 314. However, the construction of the body 302 of the example insertion tool 100 shown in FIGS. 3-5 is merely a non-limiting example. In some instances, the body 302 may be a single unitary piece. In some instances, the body 302 may include one or more cylindrical pieces. Moreover, the body 302 may be constructed in any desirable manner from any number of components.

With reference to FIGS. 3-5, the body 302 also includes reliefs 318, 319, and 320. The reliefs 318, 319, and 320 are shallow recesses formed in the body 302 to accommodate, for example, one or more fingers of a user. One or more of the reliefs 318, 319, and 320 may include a textured surface 322 that may provide a user with an improved grip of and control over the insertion tool 100. As shown in FIGS. 3 and 5, the relief 318 may include texture surface 322. However, the scope may not be so limited. Rather any, all, or none of the reliefs 318, 319, and 320 may include the textured surface 322. Similarly, the lever 304 may also include a textured surface 324. However, in some instances, the lever 304 may not include a textured surface.

Referring to FIG. 3, the nozzle 108 includes a distal tip 326 that defines an opening 328. The nozzle 108 also includes a flared portion or wound guard 330. The distal tip 326 may be adapted to be inserted into an incision formed in an eye, such as the incision 202 in eye 200 shown on FIGS. 2A and 2B, in order to deliver a folded IOL there into. The wound guard 330 may include an end surface 332 operable to contact an exterior surface in order to limit a depth to which the distal tip 326 penetrates the eye 200. In some embodiments, the wound guard 330 may be omitted.

In some embodiments, the insertion tool 100 may be preloaded. That is, the insertion tool 100 may include an IOL disposed therein when provided to an end user. In some instances, the IOL may be disposed within the insertion tool 100 in an unfolded state and ready to be delivered into a patient. Having the insertion tool 100 preloaded with an IOL reduces the number of steps a user must perform both before delivering the IOL into a patient. For example, a preloaded insertion tool obviates any steps a user would otherwise be required to perform in order to load the insertion tool with the IOL. With a reduced number of steps, error and risk associated with delivery of the IOL into a patient may be reduced. Further, an amount of time required to deliver the IOL may also be reduced. In some embodiments, the IOL may be pre-loaded into the HOMS 106.

Figure 6:
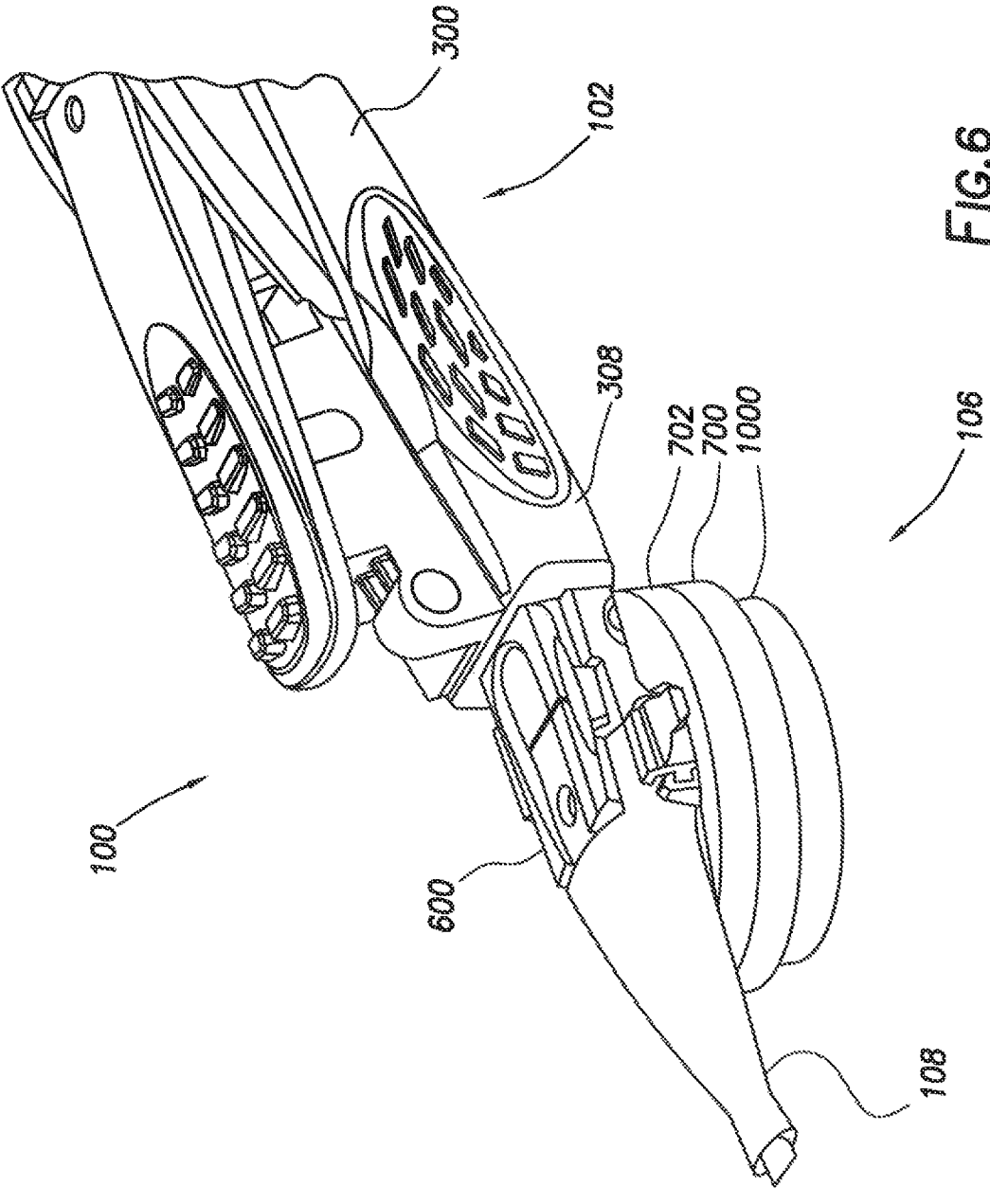
FIG. 6 is a detail view of a distal end of the insertion tool of FIG. 3.

FIG. 6 illustrates a close-up view of an example insertion tool 100 with a haptic optic management system 106. The HOMS 106 may include a first cam assembly 700, a second cam assembly 702, and a base cap 1000. The first cam assembly 700 may be disposed between the second cam assembly 702 and the base cap 1000. The HOMS 106 is operable to fold the IOL. The folded IOL may be received in housing 600 for dispending from the nozzle 108. For example, in some instances, the HOMS 106 may be operable to fold an IOL from an unstressed condition to a fully folded configuration, as shown in FIG. 1, for example. During folding, the HOMS 106 may tuck or fold the haptics 112 over the optic 114 of the IOL 110 as well as fold edges of the optic 114 over the tucked haptics 112, capturing the haptics 112 and thereby placing the IOL 110 into the folded configuration, as shown in FIG. 1, for example.

As shown in FIGS. 3-6, for example, the HOMS 106 is sized to commensurate with a size of the insertion tool 100. That is, the HOMS 106 has a compact size to avoid or limit an amount of obstruction to a surgeon's view while inserting an IOL into an eye. However, the scope of the disclosure is not so limited. Rather, in some instances, a size and/or shape of the haptic optic management system may be selected to be any desired size or shape. Further, while the HOMS 106 is shown disposed at the distal end of the insertion tool 100, the haptic optic management system 106 may be disposed anywhere within or along the insertion tool 100. In some embodiments, the HOMS 106 may be disposed between the nozzle 108 and the drive system 102.

In the illustrated example of FIGS. 3-6, the HOMS 106 is disposed between the distal end 308 of the body 302 and the nozzle 108. In some instances, the HOMS 106 may be removably coupled to the nozzle 108 and/or the drive system 102. For example, the HOMS 106 may be removable coupled to the body 302 with the use of fasteners or adhesives. In still other implementations, the HOMS 106 may couple to the body 302 by a snap-fit engagement or any other desired method of connection. Without limitation, example fasteners may include nuts and bolts, washers, screws, pins, sockets, rods and studs, hinges and/or any combination thereof.

Figure 7:
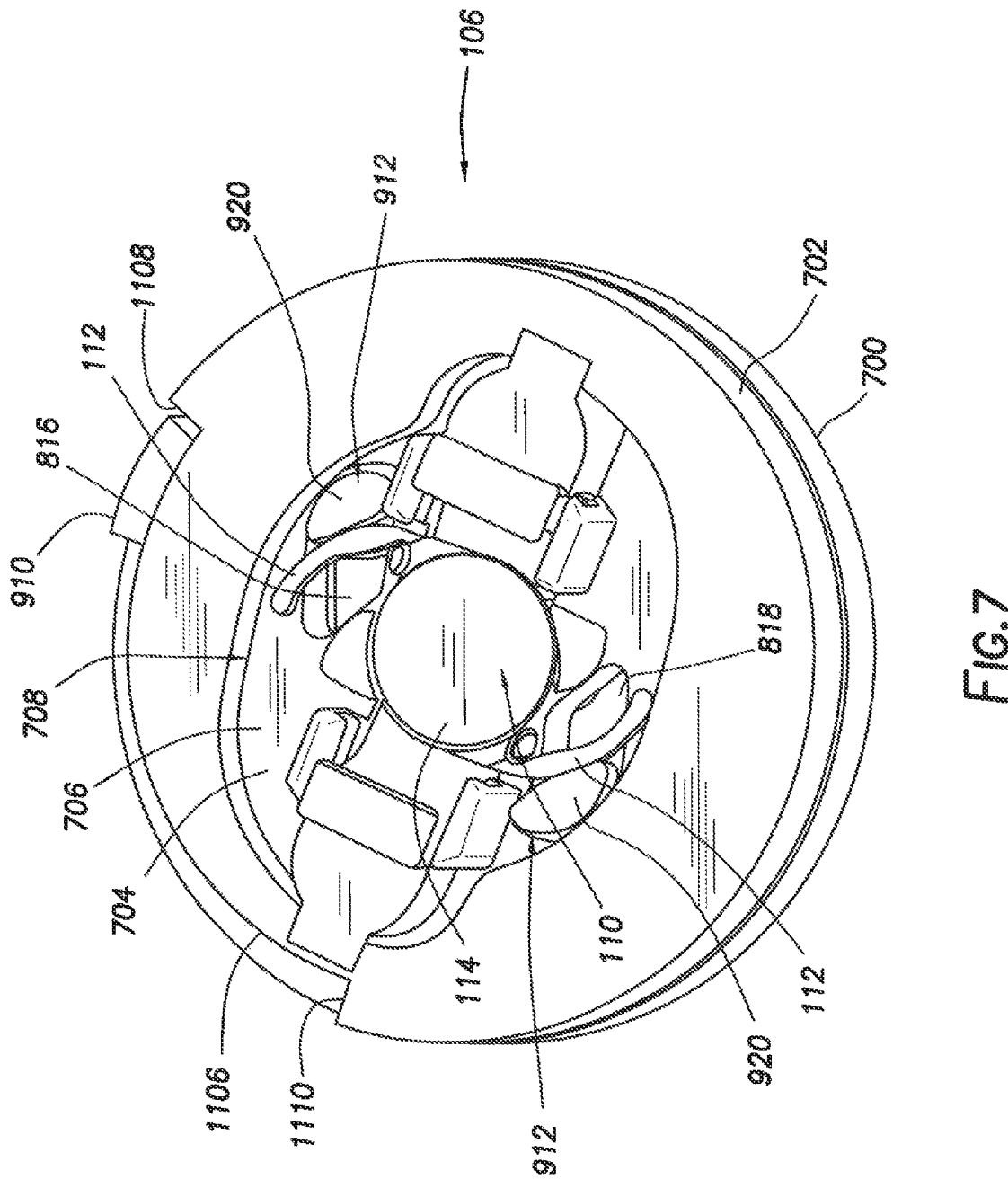
FIG. 7 illustrates an example haptic optic management.

FIG. 7 illustrates an example haptic optic management system 106. In the illustrated example, the haptic optic management system 106 includes a first cam assembly 700, a second cam assembly 702, and a central plate 704. The central plate 704 is positioned between the first cam assembly 700 and the second cam assembly 702. In examples, the central plate 704 is disposed on top of the first cam assembly 700 in a concentric fashion. As illustrated, the IOL 110 is disposed on lens face 706 of the central plate 704 in an opening 708 in the second cam assembly 702.

Figure 8:
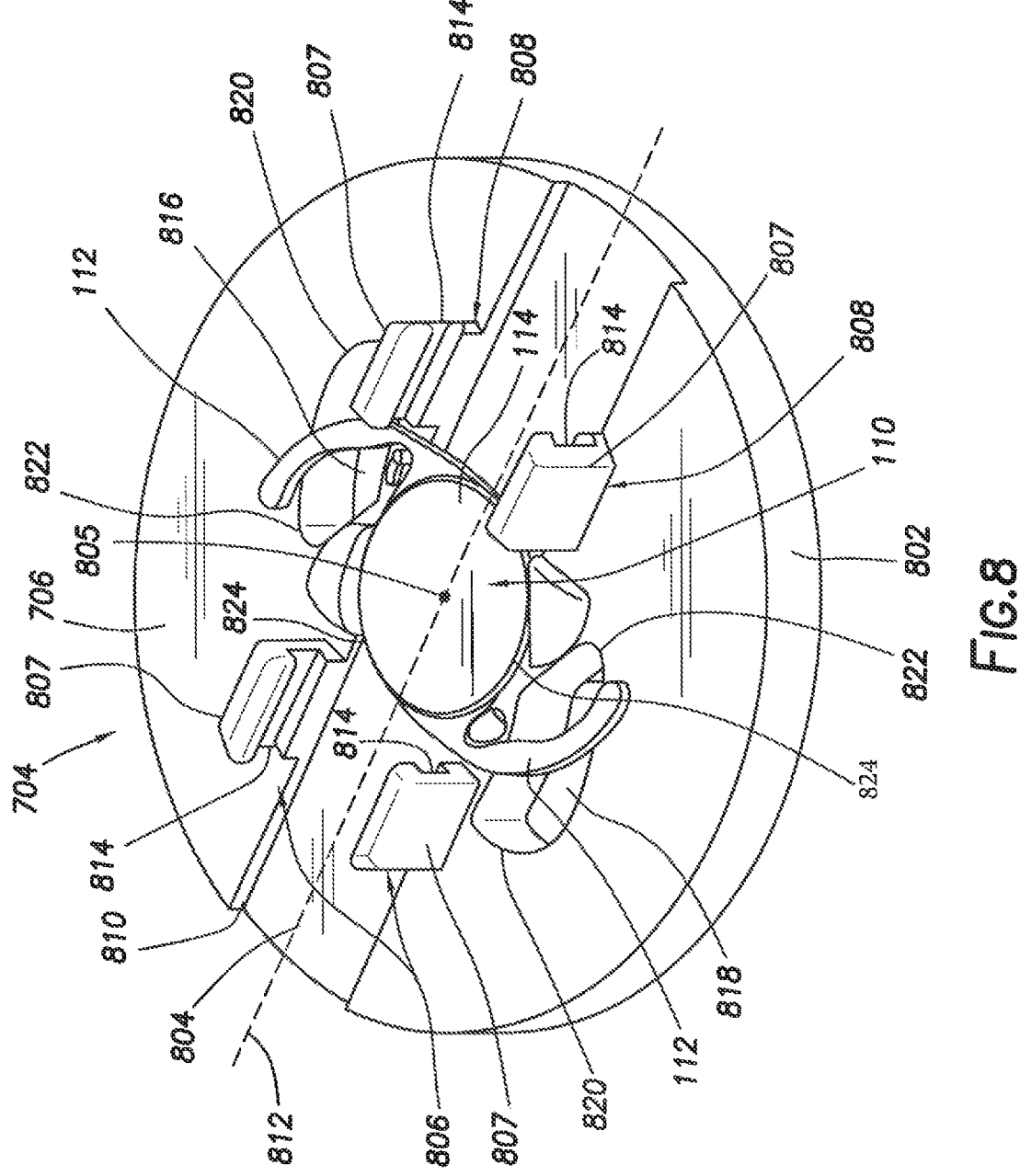
FIG. 8 illustrates a central plate of the haptic optic management system of FIG. 7.

FIG. 8 shows the central plate 704. The central plate 704 may be made from materials, such as, for example, metals, nonmetals, polymers, ceramics, and/or combinations thereof. The central plate 704 may have any suitable size and/or shape. As illustrated, the central plate 704 may disc shaped, in that the central plate 704 is generally circular in shape. However, other shapes are also contemplated. For example and without limitation, the central plate 704 may be shaped such that all or a portion of the central plate 704 is elliptical, triangular, rectangular, square, hexagonal, and/or combinations thereof. As illustrated, the central plate 704 includes a lens face 706 and an edge 802 around the perimeter of the lens face 706. In the illustrated example, a channel 804 is formed in the lens face 706. In some instances, the channel 804 extends across the entirety of the lens face 706. As illustrated, the channel 804 extends through a center 805 of the lens face 706 and along a midline 812 of the lens face 706. The channel 804 may be rectangular in cross-section, for example, but the channel 804 may be otherwise formed as desired for a particular application.

The central plate 704 further includes a first pair of guides 806 and a second pair of guides 808. In some embodiments, the first pair of guides 806 and the second pair of guides 806 are disposed on the edges 810 of the channel 804. The first pair of guides 806 and the second pair of guides 808 may be positioned on opposite sides of the IOL 110 from one another. In some embodiments, the first pair of guides 806 and the second pair of guides 806 are disposed equidistant from the center 805 of the lens face 706 of the central plate 704. In additional examples, the first pair of guides 806 is symmetric with the second pair of guides 808 in relation to the center 805. In some embodiments, the first pair of guides 806 and the second pair of guides 808 may each include opposing projections 807. The projections 807 for each of the first pair of guide 806 and the second pair of guides 808 may be on opposite sides of the channel 804. As illustrated, the projections 807 extend outwards from the lens face 706. In some embodiments, the projections 807 for each of the first pair if guides and the second pair of guides 808 may each include protrusion channels 814 facing inward toward the channel 804, as shown on FIG. 8.

Additionally, the central plate 704 includes a first opening 816 and a second opening 818. In some embodiments, the first opening 816 and the second opening 818 are positioned on either side of the channel 804. In examples, the first opening 816 and the second opening 818 each include a first end 820 and a second end 822. In some instances, the first opening 816 and the second opening 818 may be transposed across the midline 812 and the channel 804.

The central plate 704 supports the IOL 110. As illustrated, the IOL 110 is disposed on the central plate 704 and supported by the lens face 706. The IOL 110 includes haptics 112 and an optic 114. In some embodiments, the optic 114 is positioned across the channel 804 in the lens face 706 with edges 824 of the optic 114 at least partially disposed on the lens face 706. The haptics 112 extend from the optic 114 across the first opening 816 and the second opening 818. As illustrated, one of the haptics 112 extends across the first opening 816 while another of the haptics 112 extend across the second opening 818.

Figure 9:
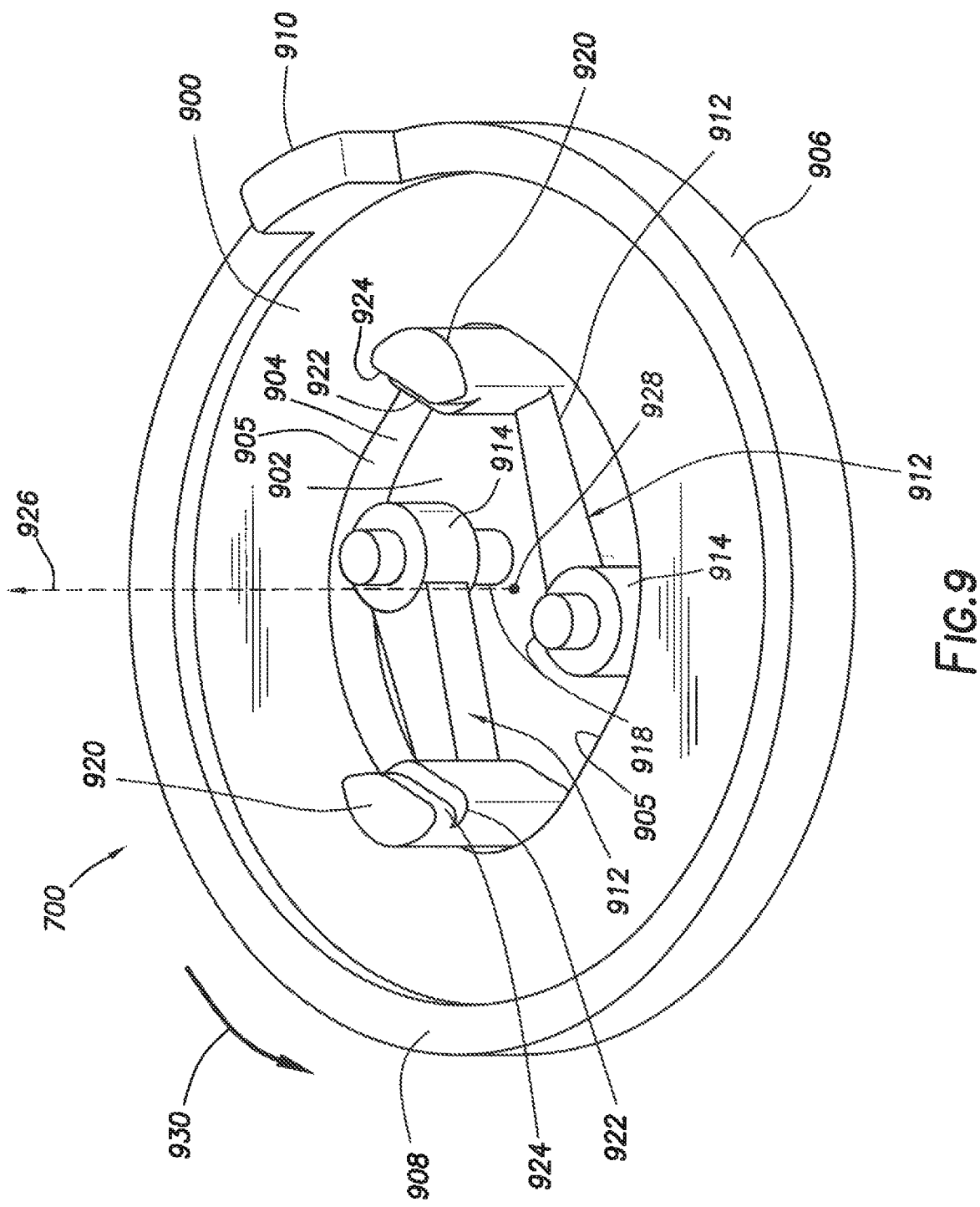
FIG. 9 illustrates a first cam assembly of the haptic optic management system of FIG. 7.

FIG. 9 shows the first cam assembly 700. The first cam assembly 700 may be made from materials, such as, for example, metals, nonmetals, polymers, ceramics, and/or combinations thereof. The first cam assembly 700 may have any suitable size and/or shape. As illustrated, the first cam assembly 700 may annular shaped, in that the central plate is generally shaped like a ring. However, other shapes are also contemplated. In the illustrated example, the first cam assembly 700 includes a first cam body portion 900 that includes an opening 902. The first cam body portion 900 further includes an inner perimeter 904 that defines the opening 902 and an outer perimeter 906. The diameter of the opening 902 is not uniform such that the diameter varies along the inner perimeter 904 defining one or more cam surfaces 905. In the illustrated embodiment, the inner perimeter 904 define two of the cam surfaces 905, but it is contemplates that there may be more or less than two of the cam surfaces 905. The first cam assembly 700 further includes a raised ring 908 along the outer perimeter 906 of the first cam body portion 900. The raised ring 908 may be raised, for example, with respect to the lens face 706. The raised ring 908 may have any suitable thickness and any suitable height above and/or below the lens face 706. The first cam assembly 700 further includes a cam projection 910. In the illustrated example, the cam projection 910 is positioned at the outer perimeter 906 and extends from the raised ring 908.

In some embodiments, the first cam assembly 700 further includes haptic folder arms 912 positioned in the opening 902. When actuated (described in more detail below), the haptic folder arms 912 causes the haptics 112 (e.g., referring to FIG. 7) to folder over on top of the optic 114 (e.g., referring to FIG. 7). Each of the haptic folder arms 912 includes a first end 914 and a second end 916. A pin 918 extends from the second end 916. The pin 918 is received in holes formed in the base cap (e.g., holes 1006 in base cap 1000 shown on FIG. 10). The haptic folder arms 912 are operable to rotate about the pin 918, in that the pin 918 is the fixed component of the haptic folder arms 912 upon which the haptic folder arms 912 rotate. The haptic folder arms 912 also include a protrusion 920 at the second end 916. The protrusion 920 is operable to engage a haptic 112 (e.g., referring to FIG. 7) of an IOL 110 (e.g., shown on FIG. 1). The protrusion 920 includes a platform 922 and a haptic engagement surface 924. The platform 922 receives the haptics 112 of the IOL 110 (e.g., referring to FIG. 7).

In some embodiments, an operator applies a force to the first cam assembly 700 (either directly or indirectly), thereby causing the first cam assembly 700 to rotate. The first cam assembly 700 may rotate about a transverse axis 926 passing through a center 928 of the first cam assembly 700. As illustrated, the first cam assembly 700 may rotate in the direction indicated by arrow 930. While the arrow 930 indicates counter-clockwise rotation, it is also contemplated that the first cam assembly 700 may also be configured for clockwise rotation. The protrusions 920 of the haptic folder arms 912 travel along the inner perimeter 904. The diameter of the inner perimeter 904 at a given location varies. As the diameter of the inner perimeter 904 varies, the protrusions 920 follow the profile of the inner perimeter 904. In some embodiments, where the opening 902 may be elliptical in shape, the protrusions 920 travel from a portion of the inner perimeter 904 with a larger diameter to a portion with a reduced diameter, in that the protrusions 920 follow the one or more cam surfaces 905 as the haptic folder arms 912 rotate.

Figure 10:
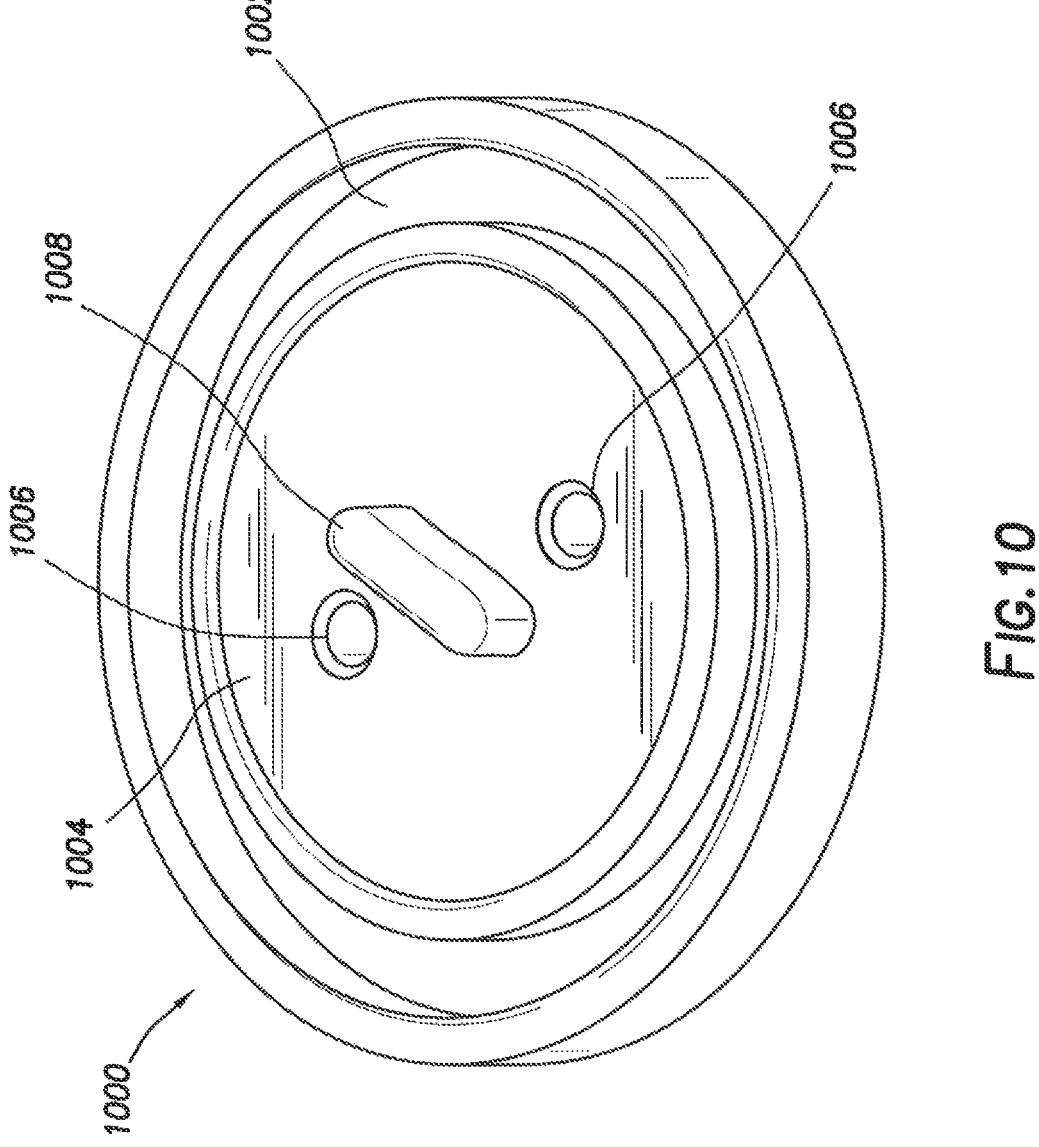
FIG. 10 illustrates a base cap of the haptic optic management system of FIG. 7.

FIG. 10 is shows a base cap 1000. The base cap 1000 may be made from materials, such as, for example, metals, nonmetals, polymers, ceramics, and/or combinations thereof. The base cap 1000 may have any suitable size and/or shape. As illustrated, the base cap 1000 may disc shaped, in that the base cap 1000 is generally circulate in shape. However, other shapes are also contemplated. For example and without limitation, the base cap 1000 may be shaped such that all or a portion of the base cap 1000 is elliptical, triangular, rectangular, square, hexagonal, and/or combinations thereof. In examples, the base cap 1000 includes a recessed ring 1002. The recessed ring 1002 may be disposed at any suitable distance from the center of the base cap 1000. As illustrated, the recessed ring 1002 defines a raised central surface 1004. In some instances, the recessed ring 1002 of the base cap 1000 receives the raised ring 908 (e.g., referring to FIG. 9) of the first cam assembly 700. In some embodiments, one or more holes 1006 are formed in the raised central surface 1004 of the base cap 1000. The one or more holes 1006 may be receive the pins 918 of the haptic folder arms 912 (e.g., referring to FIG. 9). The one or more holes 1006 may be disposed in any suitable fashion at any location on the base cap 1000. In some embodiments, the base cap 1000 also includes protrusion 1008. The protrusion 1008 may have any suitable size and/or shape. For example and without limitation, the protrusion 1008 may be shaped such that all or a portion of the protrusion 1008 may have a cross-sectional shape that is circular, elliptical, triangular, rectangular, square, hexagonal, and/or combinations thereof. The protrusion 1008 is operable to align the base cap 1000 in relation to the first cam assembly 700 and the second cam assembly 702.

Figure 11:
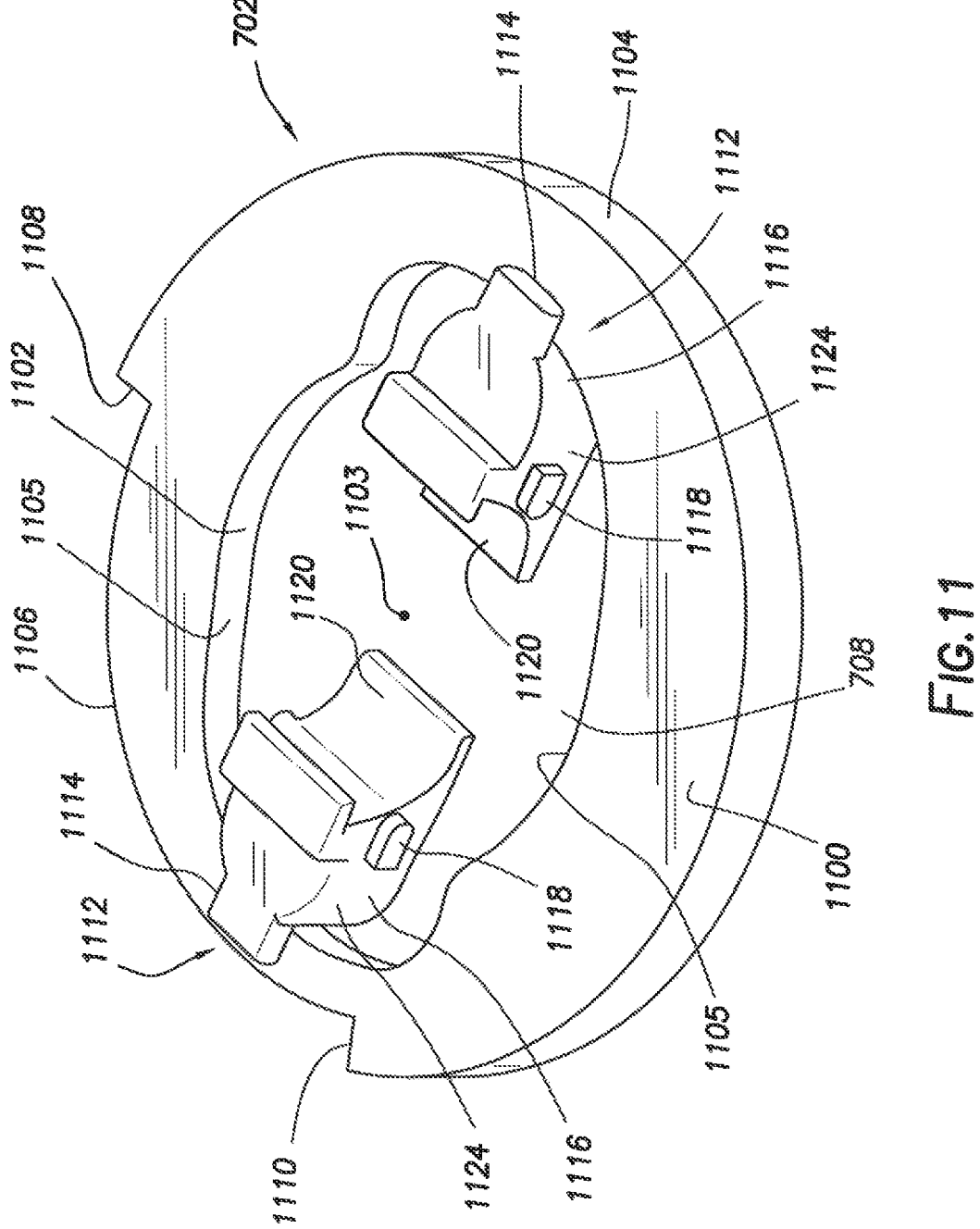
FIG. 11 illustrates a second cam assembly of the haptic optic management system of FIG. 7.

FIG. 11 is a perspective view of the second cam assembly 702. The second cam assembly 702 may be made materials, such as, for example, metals, nonmetals, polymers, ceramics, and/or combinations thereof. The second cam assembly 702 may have any suitable size and/or shape. The second cam assembly 702 may have any suitable size and/or shape. As illustrated, the second cam assembly 702 may annular shaped, in that the central plate is generally shaped like a ring. However, other shapes are also contemplated. In embodiments, the second cam assembly 702 includes a second cam body portion 1100 that includes the opening 708. The second cam body portion 1100 includes an inner perimeter 1102 that defines the opening 708 and an outer perimeter 1104. The diameter of the opening 708 is not uniform such that the diameter varies along the inner perimeter 1102 defining one or more cam surfaces 1105. In the illustrated embodiment, the inner perimeter 1102 define two of the cam surfaces 1105, but it is contemplates that there may be more or less than two of the cam surfaces 1105. The second cam assembly 702 includes a recessed portion 1106 in the outer perimeter 1104. The recessed portion 1106 serves to actuate the second cam assembly 702. The recessed portion 1106 may be a portion of the second cam assembly 702 that is missing material along the outer perimeter 1104. For example, the recessed portion 1106 includes a first end 1108 and a second end 1110 that defines the arc length of the recessed portion 1106.

As illustrated, the second cam assembly 702 further includes optic folders 1112 disposed in the opening 708. In some instances, there may be a plurality of the optic folders 1112. In the illustrated example, two of the optic folders 1112 are disposed in the opening 708. The optic folders 1112 are operable to travel along the inner perimeter 1102 of the opening 708 and in the channel 804 (e.g., shown on FIG. 8) formed in the lens face 706 of the central plate 704. In some embodiments, each of the optic folders 1112 may be operable to follow the one or more cam surfaces 1105. For example, each of the optic folders 1112 may be operable to follow a corresponding one of the cam surfaces 1105. As the inner perimeter 1102 has a diameter that varies, the optic folders 1112 should move toward a center 1103 of the second cam assembly 702 as they follow the one or more surfaces. The optic folders 1112 may be made from materials, such as, for example, metals, nonmetals, polymers, ceramics, and/or combinations thereof.

In some embodiments, the optic folders 1112 each include a tab 1114, a body portion 1116, protrusions 1118, and a ramp 1120. The tab 1114 may extend from the body portion 1116 opposite the ramp 1120 and to engage the second cam body portion 1100. The protrusion 1118 may be operable to guide the optic folders 1112 along the one or more cam surfaces 1105. be any suitable means of connecting the optic folders 1112 to the second cam body portion 1100 The protrusions 1118 may extend from either side of the body portion 1116 of each optic folder 1112. One of the protrusions 1118 for each optic folder 1112 is obstructed in FIG. 11 by a portion of the body portion 1116. The protrusions 1118 may slide in the protrusion channels 814 of the first pair of guides 806 (e.g., referring to FIG. 8) and/or the second pair of guides 808 (e.g., referring to FIG. 8). In examples, the ramp 1120 is an arcuate surface disposed at opposite side of the body portion 1116 from the tab 1114. In other implementations, the ramp 1120 may have other shapes. For example, the ramp 1120 may have a shape that is non-arcuate. The ramp 1120 is operable to engage and fold the optic 114 (e.g., referring to FIG. 7) when the optic folders 1112 are actuated.

Figure 12:
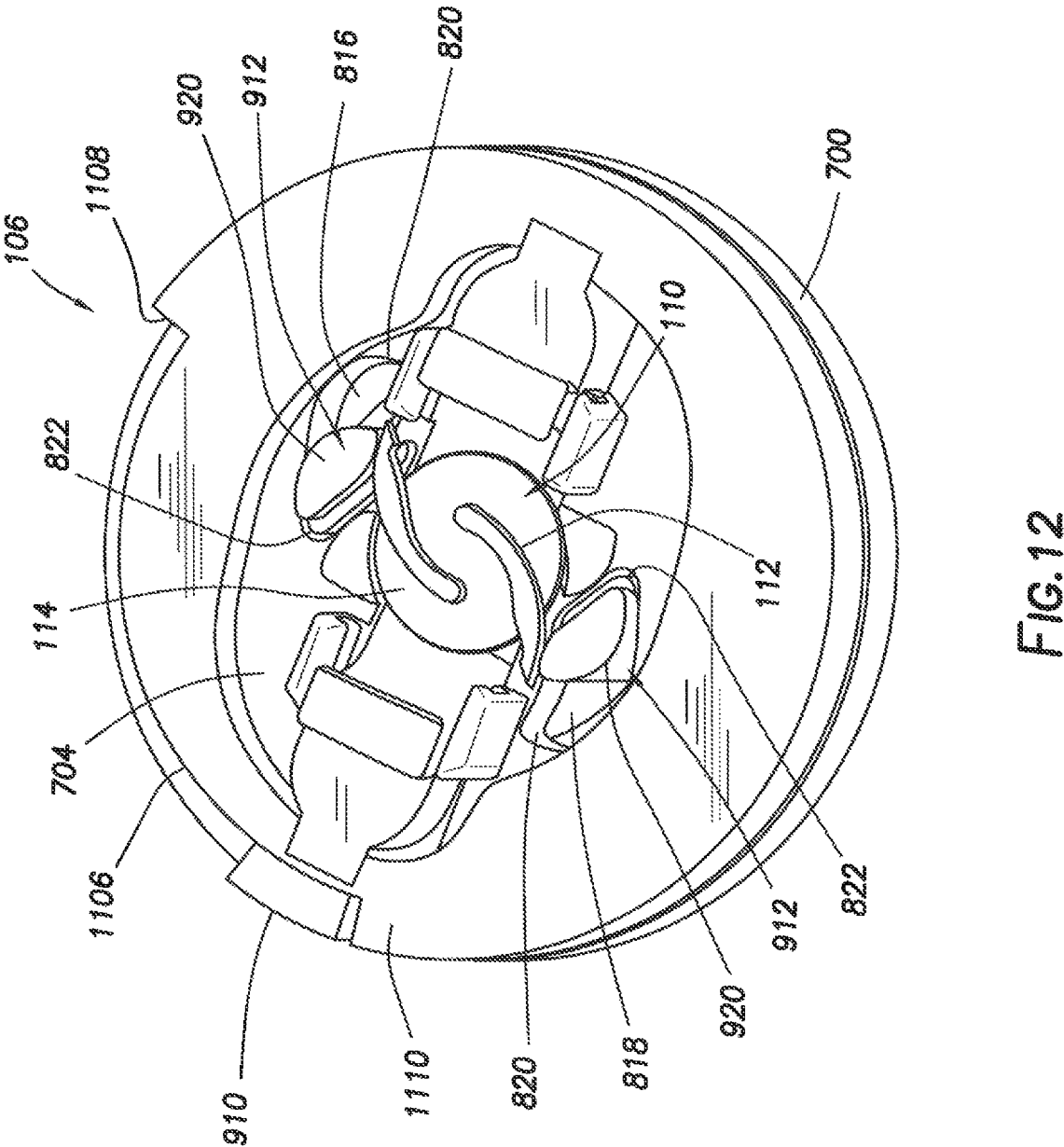
FIG. 12 illustrates the haptic optic management system of FIG. 7 in which the haptic folder arms are in an actuated position during operation thereof.

With reference now to FIGS. 7, 12, and 14, operation of the haptic optic management system will now be described. As illustrated on FIG. 7, an IOL 110 is disposed in the haptic optic management system 106. The IOL 110 may be in a relaxed or unfolded state with the haptics 112 extending from the optic 114. In the illustrated example, the IOL 110 is disposed on the central plate 704. The haptic folder arms 912 may be partially disposed through the first opening 816 and the second opening 818 in the central plate 704. In the illustrated example, the protrusions 920 of the haptic folder arms 912 are disposed within the first opening 816 and the second opening 818, respectively. As illustrated, the protrusions 920 engage the haptics 112. The cam projection 910 of the first cam assembly 700 is positioned in recessed portion 1106 of the second cam assembly 702, for example, at the first end 1108 of the recessed portion 1106. In other instances, the cam projection 910 may be otherwise positioned in the recessed portion 1106, for example, at the second end 1110.

With reference now to FIG. 12, examples include actuation of the first cam assembly 700 by rotation of the first cam assembly 700. In examples, rotation of the first cam assembly 700 actuates the haptic folder arms 912 causing the haptic folder arms 912 to pivot while folding the haptics 112 of the IOL 110 onto the optic 114. As previously described, the haptic folder arms 912 follow inner perimeter 904 (e.g., shown on FIG. 9) of the opening 902 (e.g., shown on FIG. 9), causing rotation of the haptic folder arms 912 and corresponding movement of the protrusions 920. In the illustrated example, the protrusions 920 travel from a first end 820 to a second end 822 of the first opening 816 and the second opening 818, respectively, in the central plate 704. As the first cam assembly 700 rotates, the cam projection 910 travels along recessed portion 1106. In some instances, the cam projection 910 may travel from the first end 1108 of the recessed portion 1106 to the second end 1110 of the recessed portion 1106. In some embodiments, the first cam assembly 700 may be rotated about 90° to cause the cam projection 910 to travel from the first end 1108 to the second end 1110. In other instances, the first cam assembly 700 may be rotated other distances, for example, the first cam assembly 700 may be rotated more or less than 90°.

Figure 13:
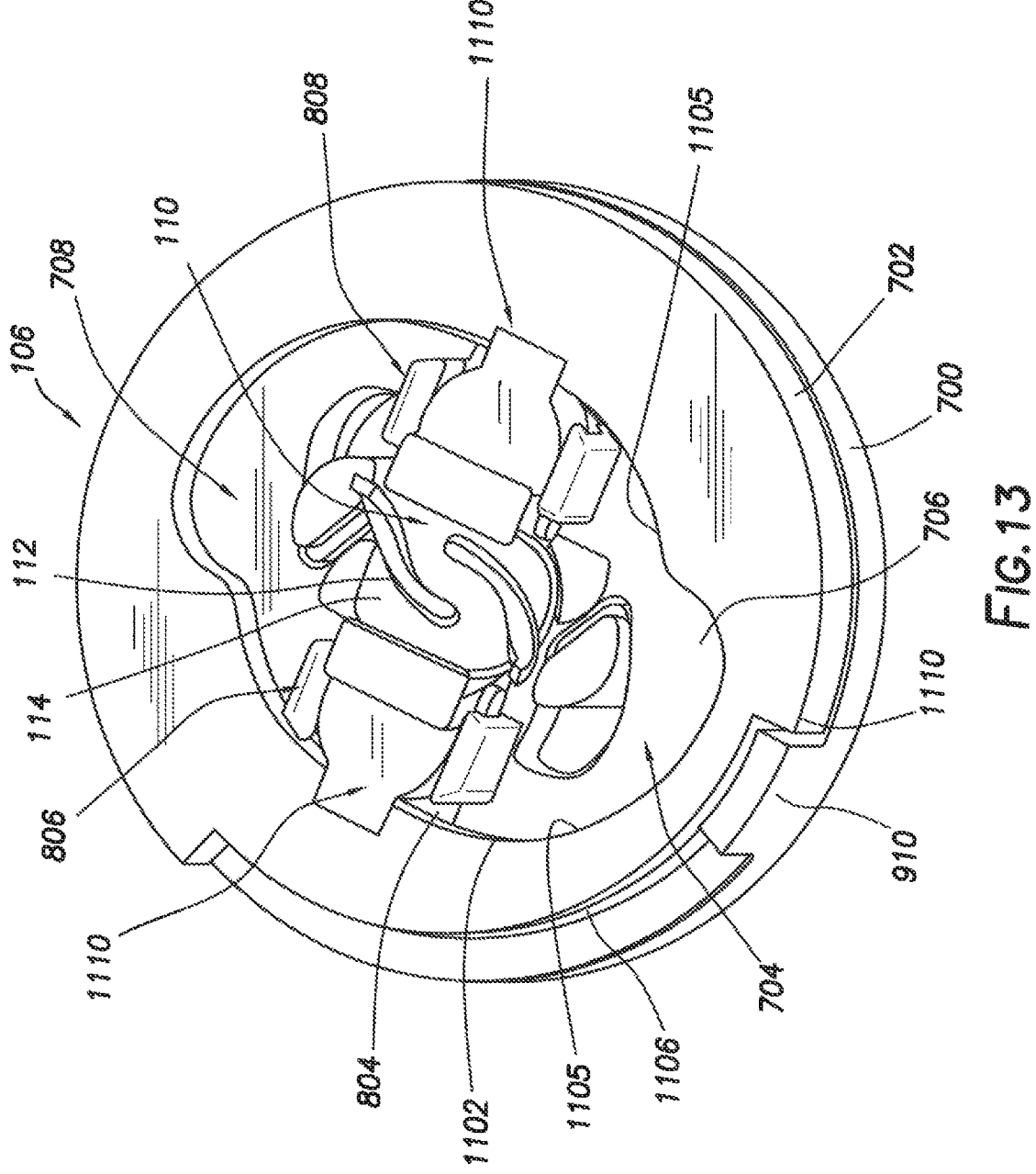
FIG. 13 illustrates the haptic optic management system of FIG. 7 in which the optic folders are in an actuated position during operation thereof.

With reference now to FIG. 13, examples include actuation of the second cam assembly 702, for example, by continued rotation of the first cam assembly 700. In examples, the first cam assembly 700 pushes against the second cam assembly 702 as the first cam assembly 700 continues to rotate. For example, the cam projection 910 engages the second end 1110 of the recessed portion 1106 to push against the second cam assembly 702, causing the second cam assembly 702 to rotate. In some embodiments, the optic folders 1112 are positioned in the opening 708 formed in the second cam assembly 702 and in the channel 804 formed in the lens face 706 of the central plate 704. As the second cam assembly 702 rotates, the optic folders 1112 follow the one or more cam surfaces 1105 formed in the inner perimeter 1102 of the opening 708. As the opening 708 reduces in diameter, the optic folders 1112 move inward along the channel 804 while engaging the optic 114. By way of example, the ramps 1120 (e.g., shown on FIG. 11) engage the optic 114. The first pair of guides 806 and the second pair of guides 808 guide the optic folders 1112 as they move inward in the channel 804. In some instances, the optic folders 1112 push against the optic 114 so as to cause the optic 114 to fold in upon itself with the haptics 112 positioned on top of the optic 114 to fold the IOL 110, such as into folded configuration 116 for the IOL 110 shown on FIG. 1. The IOL 110 may then be elevated or dropped from the opening 708 and into housing 600 (e.g., shown on FIG. 6). Any suitable technique may be used to move the IOL 110 from the opening 708 into the housing 600. A drive system, such as the drive system 102 shown on FIG. 1, may then be used to dispense the IOL 110 from the housing 600. Accordingly, the haptic optic management system 106 as described herein may be used to prepare the IOL 110 for insertion into the eye 200 (e.g., shown on FIGS. 2A and 2B).

In various embodiments, a haptic optic management system ("HOMS") can be any of a wide variety of systems, devices, components, cartridges etc. in an intraocular lens (IOL) delivery system which are configured to prepare an IOL for delivery. The HOMS can be positioned between a nozzle or tip of the IOL insertion tool and a plunger and/or drive system of the IOL insertion tool. For example, the HOMS can be a component in a multi-component, modular IOL insertion tool having one or more of a cartridge, a nozzle component, a driving mechanism component, a plunger component, a nozzle component, the HOMS component, etc. A HOMS, as described herein, can be used with either a modular IOL insertion tool, or an IOL insertion tool having permanently- or semi-permanently-coupled components. In a modular embodiment, a cartridge component including a HOMS may be coupled to a drive component. The HOMS can accept a user actuation of the HOMS system to prepare an IOL contained therein for delivery by a subsequent interaction from a plunger and/or a driving mechanism.

As described above, a HOMS can involve a system for accepting a user actuation to prepare the IOL for delivery, and can include a first and second cam assembly for tucking and/or folding the haptics of an IOL over the optic of the IOL, folding the edges of the optic over the tucked haptics, and/or capturing the haptics to place the IOL into the folded configuration for insertion through a nozzle of an IOL injector. However, depending on a material of an IOL, a shape of an IOL, the presence or lack of an interior capacity in the IOL, a material contained in an interior capacity of an IOL, etc., the HOMS can be configured to accept a user actuation in order to deform an IOL in a wide variety of configurations in preparation for being pushed through the nozzle of an IOL injector and ejected from the IOL injector.

As described above, the HOMS can be configured to deform and/or manipulate the haptics and/or the optic of an IOL into various configurations. For example, in some cases, a HOMS can be configured to extend the haptics of an IOL in substantially opposite directions away from the optic. For example, a HOMS can include a cavity for supporting a pre-loaded IOL and a cam mechanism for elongating and/or extending the haptics and/or optic of the IOL. The cam mechanism may be actuated by a user to actively deform, elongate, extend, or otherwise fold features of the IOL (e.g., fold one haptic, fold multiple haptics, deform one haptic, deform multiple haptics, extend one haptic, extend multiple haptics, etc.) before a plunger of the IOL injector contacts the IOL and before advancement of the IOL into the nozzle of the IOL insertion tool. Those of ordinary skill in the art having the benefit of this disclosure will readily appreciate that a wide variety of deformations are possible and can be achieved using the structures and principles described herein.

Although specific examples of cam assemblies are described above, for the purpose of this disclosure a cam can be any rotating or sliding component for transforming rotary motion into linear motion for manipulating one or more components of the IOL (for example, to deform, elongate, extend, or fold features of the IOL). The cam assembly may be actuated by a user via any suitable mechanism, including turning or rotating a dial, cap, or wheel on the IOL insertion tool. Alternatively, the cam mechanism may be actuated via manipulation of non-rotating features (e.g., switch, lever, slide, button, etc.) that are mechanically linked to the cam mechanism to impart appropriate rotary motion to deform, elongate, extend, or otherwise fold features of the IOL as noted above.

FIG. 14 illustrates a method 1400 for preparing an intraocular lens (IOL) for delivery via an IOL insertion tool as disclosed herein. At step 1405, a drive system of a modular IOL insertion tool may optionally be coupled to an IOL cartridge that includes a pre-loaded IOL and a haptic optic management system ("HOMS"). At step 1410, the IOL cartridge may optionally be coupled to a nozzle component of the modular IOL insertion tool. At step 1415, user actuation of the HOMS of the IOL insertion tool (e.g., via rotation of a dial) is translated to actively manipulate (e.g., deform, elongate, extend, or otherwise fold) one or more features of the pre-loaded IOL before the IOL is advanced into the nozzle component. This translation may be implemented in any suitable manner, for example as discussed in examples above. In some embodiments, the HOMS actively manipulates the IOL into a configuration suitable for advancement into the nozzle before a plunger or nozzle of the IOL insertion tool comes into contact with any features of the IOL. In this manner, the IOL may be actively folded or extended for advancement as a separate user step from engaging the drive system and/or plunger. At step 1420, a user actuation of a drive mechanism of the IOL insertion tool is translated to advance the IOL through the nozzle, and deliver the IOL into the target (e.g., an anterior capsule of a patient).

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. An intraocular lens (IOL) insertion tool, comprising:

an IOL disposed within a cavity;

a nozzle;

a plunger configured to advance the IOL through the nozzle; and a haptic optic management system (HOMS) comprising:

one or more arms;

a cam mechanism configured to translate a user actuation of the HOMS to actively deform the IOL before the IOL is advanced into the nozzle, wherein the HOMS is further configured to tuck one or more haptics of the IOL onto an optic of the IOL and to fold one or more edges of the optic of the IOL over the one or more tucked haptics of the IOL; and wherein the HOMS comprises a rotatable dial, the user actuation comprises rotating the dial, and the cam mechanism is configured to translate rotation of the dial to move the one or more arms disposed within the cavity, thereby actively deforming the IOL.

2. The IOL insertion tool of claim 1, wherein the cam mechanism of the HOMS is further configured to translate the user actuation of the HOMS to actively deform the IOL without the IOL making contact with the nozzle or the plunger.

3. The IOL insertion tool of claim 1, wherein the HOMS is further configured to elongate, in opposite directions, a pair of haptics of the IOL.

4. The IOL insertion tool of claim 3, wherein the HOMS is further configured to compress the pair of haptics when the pair of haptics are elongated.

\* \* \* \* \*